(12) United States Patent
He et al.

(10) Patent No.: US 12,266,206 B1
(45) Date of Patent: Apr. 1, 2025

(54) HAND ACUPOINT POSITIONING METHOD, DEVICE, ACUPUNCTURE ROBOT AND STORAGE MEDIUM

(71) Applicant: JIANGHAN UNIVERSITY, Hubei (CN)

(72) Inventors: Qiang He, Hubei (CN); Yi Zheng, Hubei (CN); Hongxing Zhang, Hubei (CN); Qian Tu, Hubei (CN)

(73) Assignee: JIANGHAN UNIVERSITY, Wuhan (CN)

( * ) Notice: Subject to any disclaimer, the term of this patent is extended or adjusted under 35 U.S.C. 154(b) by 0 days.

(21) Appl. No.: 18/909,970

(22) Filed: Oct. 9, 2024

(30) Foreign Application Priority Data

Jun. 19, 2024 (CN) .......................... 202410791960.8

(51) Int. Cl.
| | |
|---|---|
| *G06V 40/10* | (2022.01) |
| *A61B 34/30* | (2016.01) |
| *G06T 7/73* | (2017.01) |
| *G06V 10/26* | (2022.01) |
| *G06V 10/77* | (2022.01) |
| *G06V 10/80* | (2022.01) |
| *G06V 10/82* | (2022.01) |

(52) U.S. Cl.
CPC ............ *G06V 40/107* (2022.01); *A61B 34/30* (2016.02); *G06T 7/73* (2017.01); *G06V 10/26* (2022.01); *G06V 10/7715* (2022.01); *G06V 10/806* (2022.01); *G06T 2207/20084* (2013.01); *G06T 2207/30004* (2013.01); *G06T 2207/30196* (2013.01); *G06V 10/82* (2022.01)

(58) Field of Classification Search
CPC .......... A61B 34/30; A61H 39/02; G06T 7/73; G06T 2207/20084; G06T 2207/30004; G06T 2207/30196; G06V 10/26; G06V 10/7715; G06V 10/806; G06V 10/82; G06V 40/107

See application file for complete search history.

(56) References Cited

U.S. PATENT DOCUMENTS

2020/0126297 A1  4/2020 Tian et al.
2022/0336080 A1* 10/2022 Monteverde .............. G06T 7/70

FOREIGN PATENT DOCUMENTS

| CN | 115527235 A | 12/2022 |
|---|---|---|
| CN | 115797451 A | 3/2023 |
| CN | 117974740 A | 5/2024 |

OTHER PUBLICATIONS

Sun, Shiying, et al. "Hand acupoint detection from images based on improved hrnet." 2022 International Joint Conference on Neural Networks (IJCNN). IEEE, 2022. (Year: 2022).*

(Continued)

*Primary Examiner* — Katrina R Fujita

(57) ABSTRACT

A hand acupoint positioning method, device, acupuncture robot and storage medium, which comprises: obtaining reflex zones of a hand image and topology relationship of hand acupoints; splicing the reflex zones, the topology relationship and the hand image to obtain a hand splicing image; inputting the hand splicing image into an acupoint recognition model to obtain the hand acupoints. The invention uses reflex zones as auxiliary information and topology relationship as priority knowledge. More context information can be added to the hand acupoint positioning process, which improves the positioning accuracy of the hand acupoints.

8 Claims, 7 Drawing Sheets

(56) References Cited

OTHER PUBLICATIONS

Zheng et al. "Hybrid Attention-based Semantic Segmentation for Hand Acupoint Reflex Zones." Proceedings of the 2023 4th International Symposium on Artificial Intelligence for Medicine Science. 2023. (Year: 2023).*

Zheng et al. "Deep Learning Approach for Hand Acupoint Localization Combining Reflex Zones and Topological Keypoints." Procedia Computer Science 250 (Jul. 2024): 30-36. (Year: 2024).*

Notification to Grant Patent Right for Invention, Chinese Application No. 202410791960.8 , mailed Aug. 22, 2024 (2 pages).

CNIPA, Office Action issued for Chinese Application No. 202410791960.8, mailed Jun. 26, 2024 (17 pages).

Ning Yin et al., "Chin J Rehabil Theory Pract", Alpha-wave Cerebral Cortex Functional Networks of Magnetic Stimulation on Acupoints of Different Meridians, vol. 24, No. 12, pp. 1438-1445, date of issue Dec. 31, 2018.

* cited by examiner

HAND ACUPOINT POSITIONING METHOD, DEVICE, ACUPUNCTURE ROBOT AND STORAGE MEDIUM

FIELD OF THE DISCLOSURE

The disclosure relates to the technical field of acupoint recognition, in particular to a hand acupoint positioning method, device, acupuncture robot and storage medium.

BACKGROUND

Hand acupoints are an important part of the human meridian system, and it is an important node for the circulation of qi and blood. The accurate positioning of hand acupoints can improve the effect of physical therapy and health care.

In the existing technology, image recognition algorithms such as YOLO have been applied to realize hand acupoint positioning, which improves the efficiency and accuracy of the hand acupoints to a certain extent. However, due to the lack of textural and structural information relating to the human skin, the application of AI learning methods for the identification of acupoints remains limited, that is, the existing technology encounters challenges, resulting in a lower-than-desired accuracy in pinpointing hand acupoints.

Therefore, it is urgent to provide a hand acupoint positioning method, device, acupuncture robot and storage medium to improve the accuracy of hand acupoint positioning.

SUMMARY

In view of this, it is necessary to provide a hand acupoint positioning method, device, acupuncture robot and storage medium to solve the technical problems with lower positioning accuracy of hand acupoints in existing technologies.

In one aspect, the present invention provides a hand acupoint positioning method, comprising:
  obtaining reflex zones of a hand image and topology relationship of hand acupoints;
  splicing the reflex zones, the topology relationship and the hand image to obtain a hand splicing image;
  inputting the hand splicing image into an acupoint recognition model to obtain the hand acupoints.

In some possible implementations, obtaining reflex zones of a hand image, comprising:
  splitting the hand image based on a reflex zone segmentation model to obtain multiple initial reflex zones;
  obtaining a plurality of key points of the hand image and determining whether the plurality of initial reflex zones are accurate based on the plurality of key points;
  when the multiple initial reflex zones are accurate, the multiple initial reflex zones are taken as the reflex zones.

In some possible implementations, obtaining the topology relationship of the hand acupoints, comprising:
  obtaining multiple key points and hand acupoints of the hand image;
  determining multiple first target key points that coincide with the hand acupoints in multiple key points, and multiple second target key points that do not coincide with the hand acupoints in multiple key points;
  determining the topology relationship based on the multiple first target key points and the multiple second target key points.

In some possible implementations, the acupoint recognition model includes a feature extraction module, a feature fusion module and a detection module, wherein inputting the hand splicing image into the acupoint recognition model to obtain the hand acupoints, comprising: extracting the features at different levels of the hand splicing image based on the feature extraction module to obtain a first feature map, a second feature map and a third feature map;
  enhancing and fusing the first feature map, the second feature map and the third feature map based on the feature fusion module to obtain a first enhanced feature map, a second enhanced feature map and a third enhanced feature map;
  detecting the first enhanced feature map, the second enhanced feature map and the third enhanced feature map based on the detection module to obtain the hand acupoints.

In some possible implementations, the feature extraction module includes a first feature extraction unit, three second feature extraction units and a space pyramid pool unit, the first feature extraction unit includes a first CBS layer, a second CBS layer and a first C2F layer, and the second feature extraction unit includes a third CBS layer and a second C2F layer, wherein extracting the features at different levels of the hand splicing image based on the feature extraction module to obtain a first feature map, a second feature map and a third feature map, comprising: extracting the features of the hand splicing image based on the first feature extraction unit to obtain a initial feature map;
  extracting the initial feature map based on the first second feature extraction unit to obtain the first feature map;
  extracting the first feature map based on the second second feature extraction unit to obtain the second feature map;
  extracting the second feature map based on the third second feature extraction unit and the space pyramid pooling unit to obtain the third feature map.

In some possible implementations, the feature fusion module includes two bottom-up first feature fusion units and two top-down second feature fusion units, the first feature fusion unit includes a first upsampling layer, a first splicing layer and a third C2F layer, and the second feature fusion unit includes a fourth CBS layer, a second splicing layer and a fourth C2F layer; wherein enhancing and fusing the first feature map, the second feature map and the third feature map based on the feature fusion module to obtain the first enhanced feature map, the second enhanced feature map and the third enhanced feature map, comprising:
  fusing the third feature map and the second feature map based on the first first feature fusion unit to obtain a first fusion feature map;
  fusing the first feature map and the first fusion feature map based on the second first feature fusion unit to obtain the first enhanced feature map;
  fusing the first enhanced feature map and the first fusion feature map based on the first second feature fusion unit to obtain the second enhanced feature map;
  fusing the third feature map and the second enhanced feature map based on the second second feature fusion unit to obtain the third enhanced feature map.

In some possible implementations, the detection module includes a parallel first detection unit, a second detection unit and a detection splicing unit, the first detection unit includes a fifth CBS layer and a first convolutional layer, and the second detection unit includes a sixth CBS layer and a second convolutional layer, the loss function of the first detection unit is VFL loss function, and the loss function of the second detection unit is CIoU and DFL Loss function.

In another aspect, the present invention provides a hand acupoint positioning device, comprising:

prior information acquisition unit, is used to obtain reflex zones of a hand image and the topology relationship of hand acupoints;

image splicing unit, is used to splice the reflex zones, the topology relationship and the hand image to obtain a hand splicing image;

acupoint recognition unit, is used to process the hand splicing image with the acupoint recognition model to obtain hand acupoints.

In another aspect, the invention provides an acupuncture robot, comprising memory and processor, among which, the memory is used to store a program;

the processor, coupled with the memory, is used to execute the program stored in the memory to implement the steps in the hand acupoint positioning method described in any of the possible implementations.

In another aspect, the invention provides a computer-readable storage medium is used to store a computer-readable program or instruction that, when executed by the processor, is capable of fulfilling the steps in the hand acupoint positioning method described in any of the possible implementations.

Using the above embodiments has the beneficial effects: through splicing the acquired reflex zones and topological relationship with the hand image of the unpositioned acupoint, the hand splicing image is obtained, and then the hand point is identified based on the hand part splicing image of the acupoint recognition model. Compared with the method of directly identifying the hand part image based on the acupoint recognition model, the reflex zones are taken as auxiliary information and the topological relationship is taken as prior knowledge. More contextual information can be added in the process of hand acupoint localization, which improves the accuracy of hand acupoint localization. Moreover, for the hand acupoints without obvious features or in blurred images, it can also achieve accurate recognition.

BRIEF DESCRIPTION OF THE FIGURES

To describe the technical solutions in embodiments of the present invention more clearly, the following briefly introduces the accompanying drawings for describing the embodiments. Apparently, the accompanying drawings in the following description show merely some embodiments of the present invention, and those skilled in the art may still derive other accompanying drawings from these accompanying drawings without making creative efforts.

DETAILED DESCRIPTION

The following clearly and completely describes the technical solutions in the embodiments of the present invention with reference to the accompanying drawings in the embodiments of the present invention. Apparently, the embodiments described are merely a part rather than all of the embodiments of the present invention. Based on the embodiments in the present invention, all other embodiments obtained by those skilled in the art without making creative efforts shall fall within the scope of protection of the present invention.

It should be understood that the schematic drawings are not drawn in proportion to physical objects. Flowcharts used in the present invention show operations implemented according to some embodiments of the present invention. It should be understood that the operations of the flowcharts can be implemented out of order, and the steps without a logical contextual relationship may be implemented in reverse order or implemented at the same time. In addition, under the guidance of the content of the present invention, those skilled in the art can add one or more other operations to each flowchart, and can also remove one or more operations from each flowchart. Some of block diagrams shown in the accompanying drawings are functional entities and do not necessarily have to correspond to physically or logically separate entities. These functional entities may be implemented in software, or implemented in one or more hardware modules or integrated circuits, or implemented in different network and/or processor systems and/or microcontroller systems.

The description of "first", "second", etc. involved in the embodiments of the present invention are for descriptive purposes only, and cannot be understood to indicate or imply relative importance or implicitly indicate the quantity of indicated technical features. Therefore, the technical features defined by "first" and "second" may explicitly or implicitly include at least one such feature.

The reference to "embodiments" herein means that a particular feature, structure, or characteristic described with reference to the embodiments may be included in at least one embodiment of the present invention. The appearances of the phrases in various place in the specification may not refer to a same embodiment, or an independent or a candidate embodiment that is mutually exclusive of other embodiments. Those skilled in the art explicitly and implicitly understand that the embodiments described herein may be combined with other embodiments.

The present invention provides a hand acupoint positioning method, device, acupuncture robot and storage medium which are described separately.

Figure 1:
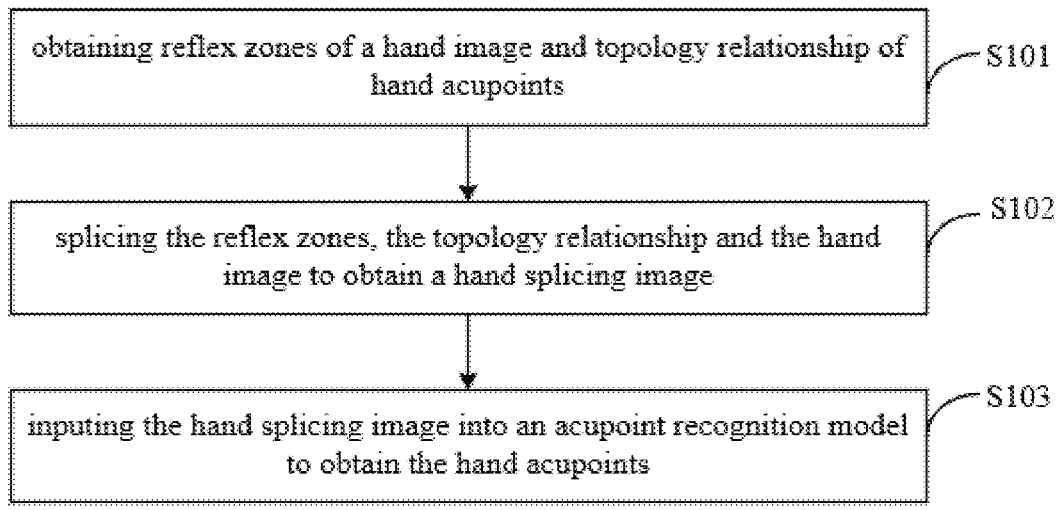
FIG. 1 is a schematic diagram of an implementation of a hand acupoint positioning method.

FIG. 1 is a schematic diagram of an implementation of a hand acupoint positioning method, as shown in FIG. 1, the hand acupoint positioning method comprises:

S101, obtaining reflex zones of a hand image and topology relationship of hand acupoints;

S102, splicing the reflex zones, the topology relationship and the hand image to obtain a hand splicing image;

S103, inputing the hand splicing image into an acupoint recognition model to obtain the hand acupoints.

Among them, the reflex zones in S101 refers to the areas with at least one acupoint, and each reflex zone corresponds to some human organs in the human body.

Specifically, the reflex zones includes the chest respiratory area, the stomach, the spleen and the large intestine area, the ear and the pharynx area, the palm area, the three acupuncture areas, the foot and leg area, the Jingxin area, the reproductive area, the palm area, lung meridian, large intestine meridian, pericardial meridian, triocale, and small intestine meridian.

Among them, the chest respiratory area includes Shaoshang point, Taiyuan acupoint, and Yuji acupoint.

Among them, the topology relationship in the S101 refers to the position constraint relationship of the acupoint, indicating that the image elements have nothing to do with the position, and there is a connection and adjacent properties on the space.

Among them, acupoint recognition models in step S103 can be a target detection model, such as: Deeplabv3+, YOLOV8, etc.

Compared with the prior art, hand acupoint positioning method provided by the embodiment of the present invention, through splicing the acquired reflex zones and topological relationship with the hand image of the unpositioned acupoints, the hand splicing image is obtained, and then the hand point is identified based on the hand part splicing image of the acupoint recognition model. Compared with the method of directly identifying the hand part image based on the acupoint recognition model, the reflex zones are taken as auxiliary information and the topological relationship is taken as prior knowledge. More contextual information can be added in the process of hand acupoint localization, which improves the accuracy of hand acupoint localization. Moreover, for the hand acupoints without obvious features or in blurred images, it can also achieve accurate recognition.

Further, because the topology relationship has nothing to do with the position, it can achieve accurate behavior of the hand acupoints between any posture and different people.

Figure 2:
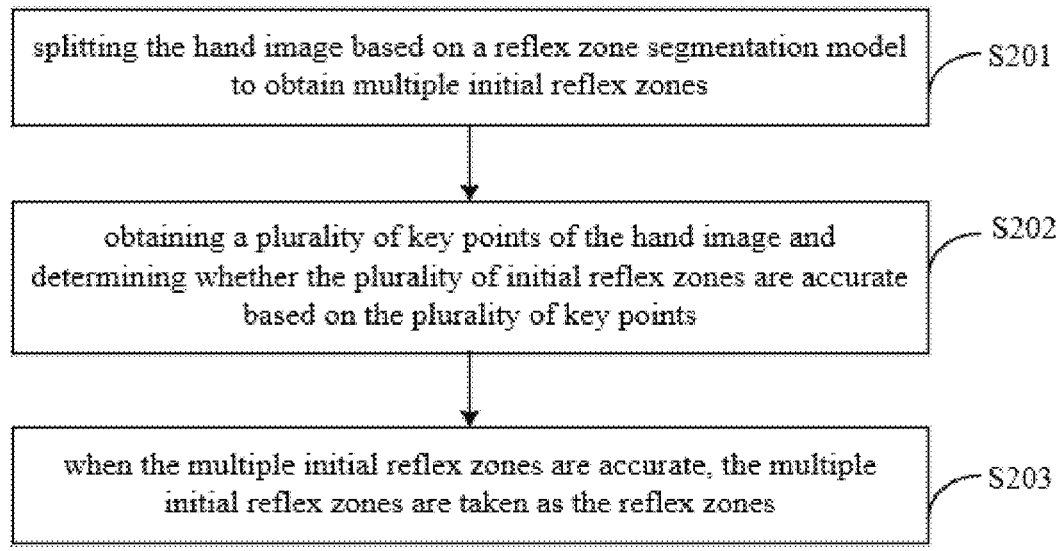
FIG. 2 is a schematic diagram of an implementation of obtaining the reflex zones of the hand image in step S101.

It can be seen from S101 S103 that accurate reflex zones will improve the accuracy of position of hand acupoints. Therefore, in order to ensure the accuracy of reflex zones, in some embodiments of the invention, as shown in FIG. 2, obtaining reflex zones of a hand image in S101, comprising:

S201, splitting the hand image based on a reflex zone segmentation model to obtain multiple initial reflex zones;

S202, obtaining a plurality of key points of the hand image and determining whether the plurality of initial reflex zones are accurate based on the plurality of key points;

S203, when the multiple initial reflex zones are accurate, the multiple initial reflex zones are taken as the reflex zones.

The implementations of the invention verifies the accuracy of the initial reflex zones through the key points. When the initial reflex zones are accurate, it is taken as the reflex zones to ensure the accuracy of the reflex zones and further improve the positioning accuracy of the hand acupoints.

The reflex zone segmentation model in S201 can be any of the existing target detection models, such as DeeplabV3+, SSD and RetinaNet.

The key points in S202 can be obtained as follows: key points can be obtained based on the MediaPipe key point detection algorithm. In the specific implementations of the invention, a total of 21 key points are determined by the MediaPipe key point detection algorithm, and the numbering, names and corresponding positions of the 21 key points are shown in Table 1.

TABLE 1

| key points | |
|---|---|
| numbering, names | corresponding positions |
| 0 wrist | key point in the wrist area, marking the starting position of the hand |
| 1 root of thumb | where the thumb joins the palm of the hand |
| 2 first joint of thumb | the first joint of the thumb, starting at the root of the thumb |
| 3 second joint of thumb | the second joint of the thumb, starting at the root of the thumb |
| 4 fingertip of thumb | the end point of the thumb |
| 5 root of forefinger | where the forefinger joins the palm of the hand |
| 6 first joint of forefinger | the first joint of the forefinger, starting at the root of the forefinger |
| 7 second joint of forefinger | the second joint of the forefinger, starting at the root of the forefinger |
| 8 fingertip of forefinger | the end point of the forefinger |
| 9 root of middle finger | where the middle finger joins the palm of the hand |
| 10 first joint of middle finger | the first joint of the middle finger, starting at the root of the middle finger |
| 11 second joint of middle finger | the second joint of the middle finger, starting at the root of the middle finger |
| 12 fingertip of middle finger | the end point of the middle finger |
| 13 root of ring finger | where the ring finger joins the palm of the hand |
| 14 first joint of ring finger | the first joint of the ring finger, starting at the root of the ring finger |
| 15 second joint of ring finger | the second joint of the ring finger, starting at the root of the ring finger |
| 16 fingertip of ring finger | the end point of the ring finger |
| 17 root of little finger | where the little finger joins the palm of the hand |
| 18 first joint of little finger | the first joint of the little finger, starting at the root of the little finger |
| 19 second joint of little finger | the second joint of the little finger, starting at the root of the little finger |
| 20 fingertip of little finger | the end point of the little finger |

The specific way to determine whether the plurality of initial reflex zones are accurate in S202 is as follows: determine the theoretical key points in the initial point reflex zones, and determine the actual key points in the initial point reflex zones based on multiple key points. By checking whether the number and location of the theoretical key points and the actual key points are the same, if they are the same, the initial point reflex zones are accurate; if they are not, it is inaccurate, and the reflex zone segmentation model needs to be trained again.

Figure 3:
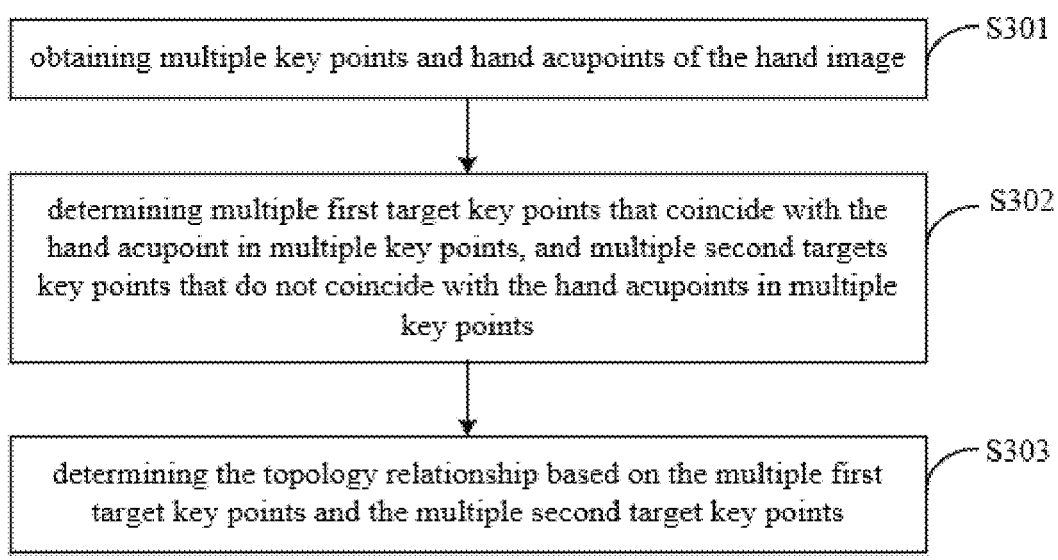
FIG. 3 is a schematic diagram of an implementation of obtaining the topology relationship of the hand acupoints in step S101.

In some embodiments of the invention, as shown in FIG. 3, obtaining the topology relationship of the hand acupoints in S101, comprising:

S301, obtaining multiple key points and hand acupoints of the hand image;

S302, determining multiple first target key points that coincide with the hand acupoint in multiple key points, and multiple second target key points that do not coincide with the hand acupoints in multiple key points;

S303, determining the topology relationship based on the multiple first target key points and the multiple second target key points.

S303 is specifically: the position of the hand acupoint is represented by the location of multiple first target key points and multiple second target key points, and this representation relationship is the topology relationship Specifically, based on the key point numbers in Table 1, the topology relationship is shown in Table 2:

TABLE 2

| acupoint name | topology relationship position |
|---|---|
| Daling acupoint | Number0 key point |
| Yuji acupoint | Number1 key point |
| Small intestine acupoint | Number6 key point |
| Large intestine acupoint | Number7 key point |
| Sanjiao acupoint | Number10 key point |
| Heart acupoint | Number11 key point |
| Liver acupoint | Number14 key point |
| Lung acupoint | Number15 key point |
| Mingmen acupoint | Number18 key point |
| Kidney acupoint | Number19 key point |
| Shaoshang acupoint | Half an inch to the left of number3 key point |
| Laogong acupoint | Make extension lines for number10 key point and number9 key point, and take the distance between number10 key point and number11 key point |
| Zhongchong acupoint | Number12 key point takes a quarter of the length of the line segment between number11 key point and number12 key point for the endpoints |
| Shaofu acupoint | Make extension lines for number18 key point and number17 key point, and take the distance between number18 key point and |
| Taiyuan acupoint | Take half the length of the line segment between number2 key point and number1 key point on the reverse extension lines of number2 key point and number1 key point |
| Shenmen acupoint | The length of Taiyuan acupoint and number0 key point is taken on the extension line of Taiyuanacupoint and number0 key point |

As can be seen from Table 2, topology relationship refers to the position relationship between key points and hand acupoints.

The key points in S301 are obtained in the same way as the key points in S202.

Figure 4:
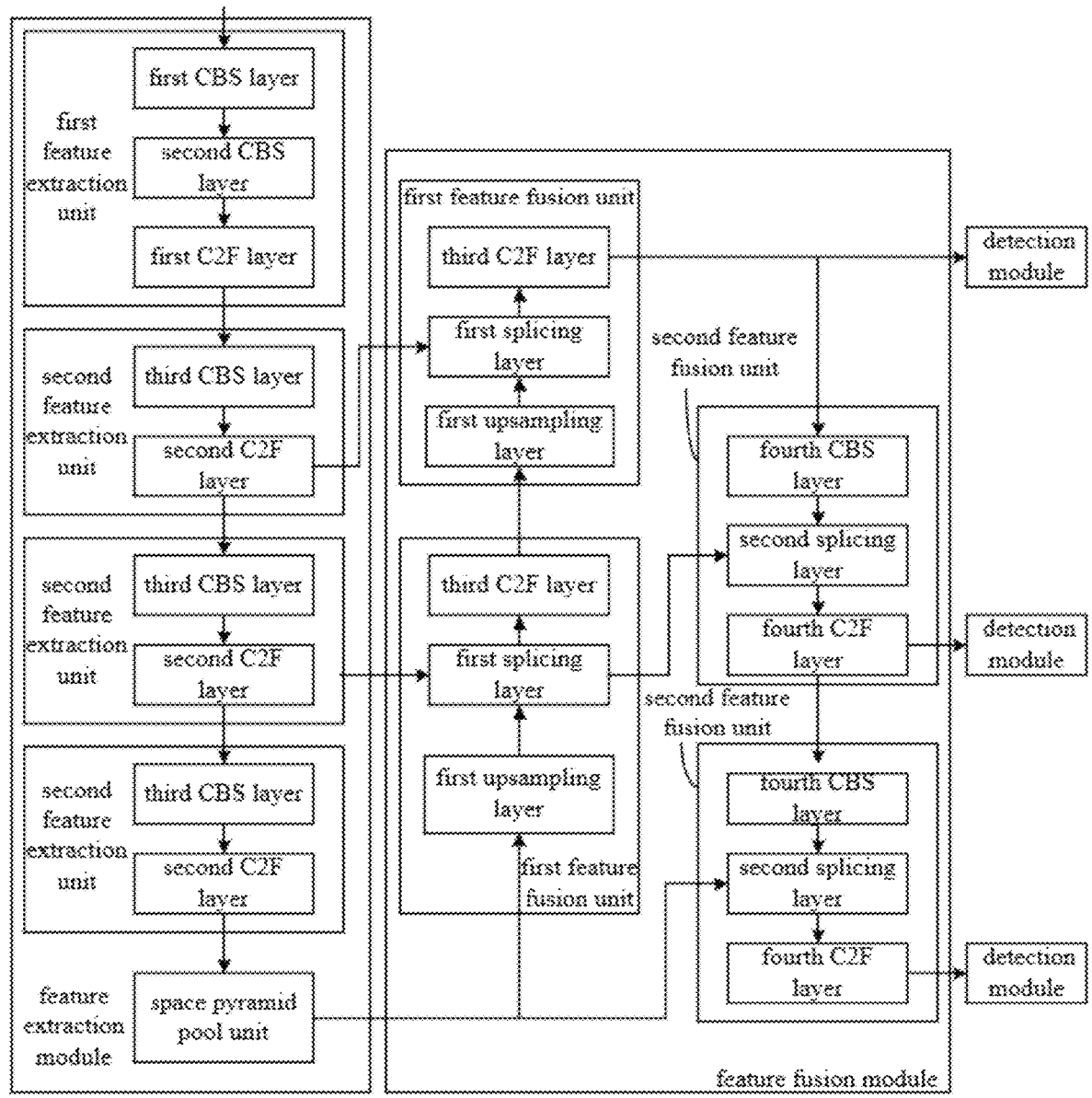
FIG. 4 is a structure diagram of an implementation of the acupoint recognition model.
Figure 5:
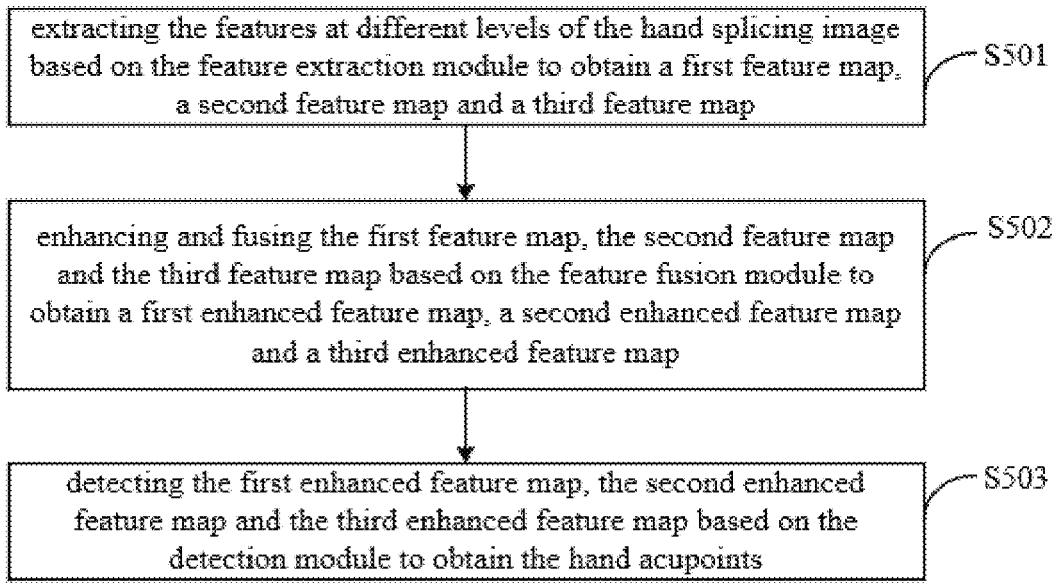
FIG. 5 is a schematic diagram of an implementation of step S103.

In the implementation of the invention, as shown in FIG. 4, the acupoint recognition model includes feature extraction module, feature fusion module and detection module, as shown in FIG. 5, inputing the hand splicing image into the acupoint recognition model, and getting the hand acupoints in S103, comprising:

S501, extracting the features at different levels of the hand splicing image based on the feature extraction module to obtain a first feature map, a second feature map and a third feature map;

S502, enhancing and fusing the first feature map, the second feature map and the third feature map based on the feature fusion module to obtain a first enhanced feature map, a second enhanced feature map and a third enhanced feature map;

S503, detecting the first enhanced feature map, the second enhanced feature map and the third enhanced feature map based on the detection module to obtain the hand acupoints.

The number of detection modules is 3, and the first enhanced feature map, the second enhanced feature map and the third enhanced feature map are respectively detected. The three detection modules output the detection result graphs with resolution of 80×80, 40×40 and 20×20 respectively.

Due to the small area of the hand acupoints, in order to achieve the detection of this smaller target, in some implementations of the invention, the feature fusion module is also used to obtain a fourth enhanced feature map in addition to the first enhanced feature map, the second enhanced feature map and the third enhanced feature map. Correspondingly, the detection module is set to 4, one of which is used to detect the fourth enhanced feature map. The detection result map with a resolution of 160×160 was obtained to improve the accurate detection of acupoints.

Figure 6:
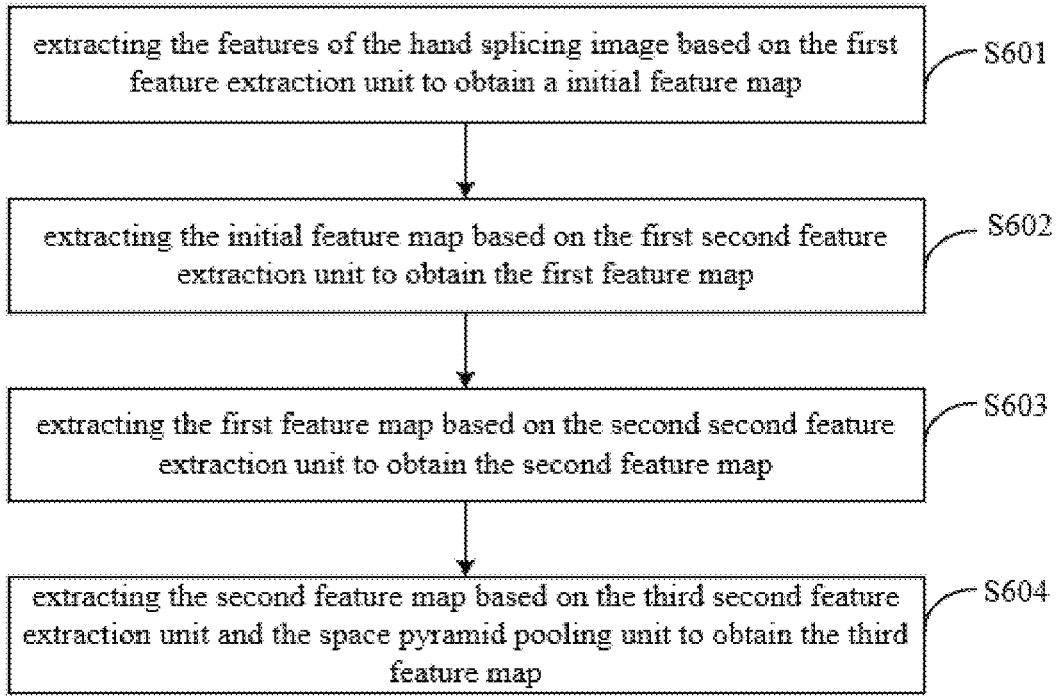
FIG. 6 is a schematic diagram of an implementation of step S501.

In some implementations of the invention, as shown in FIG. 5, the feature extraction module includes a first feature extraction unit, three second feature extraction units and a space pyramid pool unit, the first feature extraction unit includes a first CBS layer, a second CBS layer and a first C2F layer, and the second feature extraction unit includes a third CBS layer and a second C2F layer, as shown in FIG. 6, extracting the features at different levels of the hand splicing image based on the feature extraction module to obtain a first feature map, a second feature map and a third feature map, in S501, comprising: S601, extracting the features of the hand splicing image based on the first feature extraction unit to obtain a initial feature map;

S602, extracting the initial feature map based on the first second feature extraction unit to obtain the first feature map;

S603, extracting the first feature map based on the second second feature extraction unit to obtain the second feature map;

S604, extracting the second feature map based on the third second feature extraction unit and the space pyramid pooling unit to obtain the third feature map.

It should be understood that the hierarchical structure and principle of the first CBS layer, the second CBS layer and the third CBS layer are the same, and the hierarchical structure and principle of the first C2F layer and the second C2F layer are the same.

Figure 7:
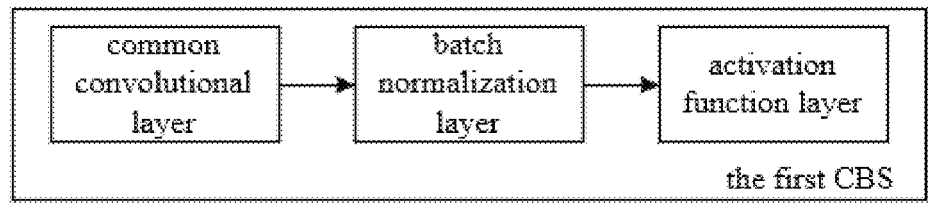
FIG. 7 is a structure diagram of an implementation of the first CBS.

As shown in FIG. 7, the first CBS layer consists of a common convolutional layer, a batch normalization layer and an activation function layer, which is used to carry out convolution operations on input data and realize the conversion and extraction of input features. The common convolutional layer is used to extract local spatial information from input feature. The role of the batch normalization layer is to normalize the output of the convolutional layer to standardize the feature value distribution in the neural network and improve the generalization ability of the network and reduce the dependence of the model on initialization. The activation function is a nonlinear function, which transforms the output of the convolution layer, changes the continuous input into the discrete output, and enhance the expression ability of the model.

The activation function is SiLU.

Figure 8:
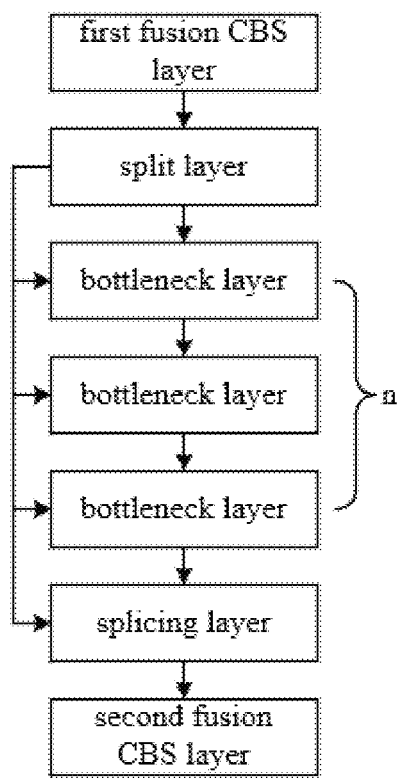
FIG. 8 is a structure diagram of an implementation of the first C2F layer.

Specifically, as shown in FIG. 8, the first C2F layer includes a first fusion CBS layer, a split layer, n bottleneck layers, a splicing layer, and a second fusion CBS layer.

The first fusion CBS layer and the second fusion CBS layer have the same structure and principle as the first CBS layer, and their names are different only to indicate that they are not the same mode layer.

In order to further improve the detection accuracy and accuracy of the acupoint recognition model for the small target of acupoints, in some implementations of the invention, the first C2F layer also includes an Efficient Multi-Scale Attention (EMA) layer connected after the second fusion CBS layer.

EMA learns efficient channel descriptions in convolution operations without reducing channel dimensions and produces better pixel-level attention for high-level feature maps. The implementations of the invention adds EMA to the feature extraction module, which significantly enhances the feature expression ability, reduces the impact of irrelevant information on features, enables the model to learn more effective information in the feature map, enhances the information expression ability of the feature map, and significantly improves the detection effect of small and densely distributed targets. The accuracy of position of hand acupoints was further improved.

Figure 9:
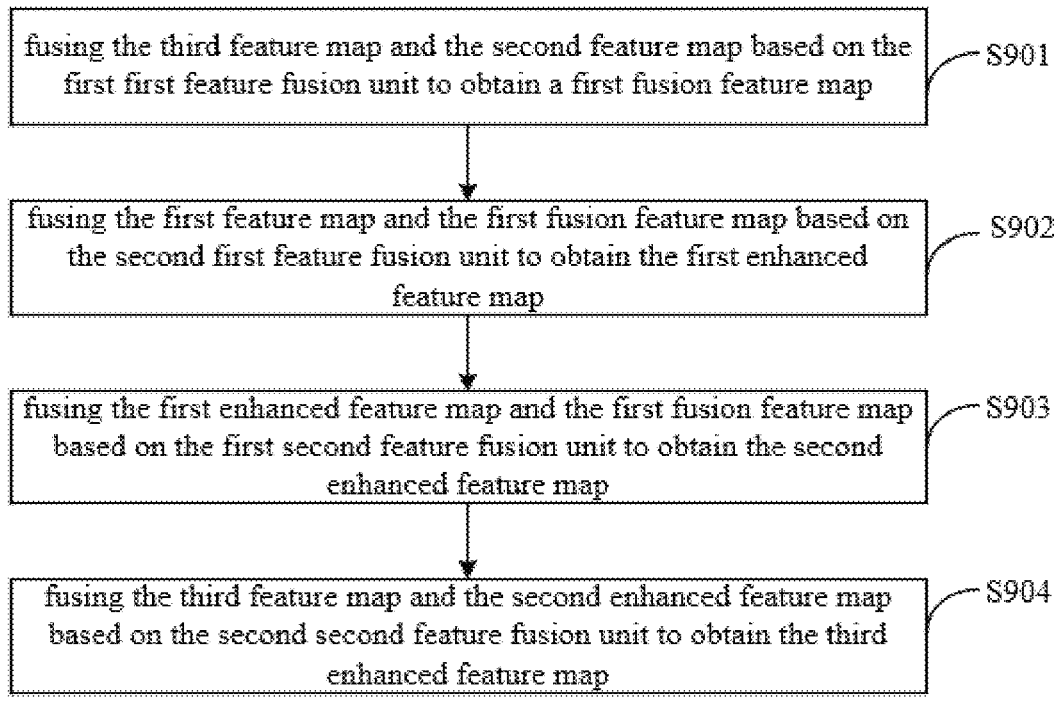
FIG. 9 is a schematic diagram of an implementation of step S502.

In some implementations of the invention, as shown in FIG. 4, the feature fusion module includes two bottom-up first feature fusion units and two top-down second feature fusion units, the first feature fusion unit includes a first upsampling layer, a first splicing layer and a third C2F layer, and the second feature fusion unit includes a fourth CBS layer, a second splicing layer and a fourth C2F layer; As shown in FIG. 9, enhancing and fusing the first feature map, the second feature map and the third feature map based on the feature fusion module to obtain a first enhanced feature map, a second enhanced feature map and a third enhanced feature map in S502, comprising:

S901, fusing the third feature map and the second feature map based on the first first feature fusion unit to obtain a first fusion feature map;

S902, fusing the first feature map and the first fusion feature map based on the second first feature fusion unit to obtain the first enhanced feature map;

S903, fusing the first enhanced feature map and the first fusion feature map based on the first second feature fusion unit to obtain the second enhanced feature map;

S904, fusing the third feature map and the second enhanced feature map based on the second second feature fusion unit to obtain the third enhanced feature map.

By setting bottom-up first feature fusion units and top-down second feature fusion units, the two-stage feature fusion strategy effectively improves the detection accuracy of the model for objects of different sizes, and enhances the ability of the network to process multi-scale information by adjusting the mode of feature fusion, and can fully fuse multi-scale information. Further ensure the positioning accuracy of the hand acupoints.

It should be noted that if the feature fusion module is also used to obtain a fourth enhanced feature map, the feature fusion module must include three bottom-up first feature fusion units and three top-down second feature fusion units. Specifically, the workflow of the first first feature fusion unit and the second first feature fusion unit remains unchanged, and the third first feature fusion unit fuses the second enhanced feature map with the initial feature map to obtain the fourth enhanced feature map.

The first second feature fusion unit fuses the fourth enhanced feature map and the first enhanced feature map to obtain the second enhanced feature map. The second second feature fusion unit fuses the first fusion feature map and the second enhanced feature map to obtain the third enhanced feature map, and the third second feature fusion unit fuses the third enhanced feature map and the third enhanced feature map.

Figure 10:
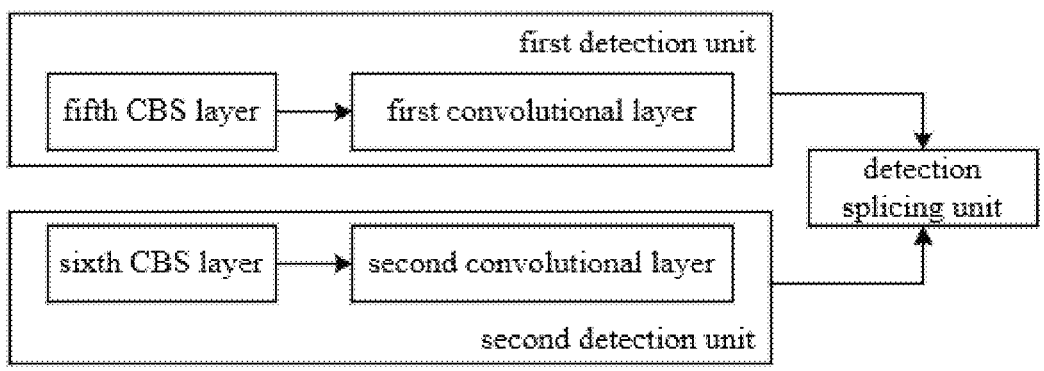
FIG. 10 is a structure diagram of an implementation of the detection module.

In some implementations of the invention, as shown in FIG. 10, the detection module includes a parallel first detection unit, a second detection unit and a detection splicing unit, the first detection unit and second detection unit are used for classification and regression, respectively.

The first detection unit includes a fifth CBS layer and a first convolutional layer, and the second detection unit includes a sixth CBS layer and a second convolutional layer, the loss function of the first detection unit is VFL loss function, and the loss function of the second detection unit is CIoU and DFL Loss function.

In order to verify the effectiveness and superiority of the hand acupoint positioning method proposed in the implementations of the invention, comparing the method that incorporates the reflex zones and topology relation with the hand acupoint positioning method that does not incorporate the reflex zones and topology relation, the comparison results show that after the method proposed in the implementations of the invention is used to treat the Yuji acupoint, Shaoshang acupoint and Taiyuan acupoint, the positioning errors of the three hand acupoints are reduced by 0.526 mm, 0.484 mm and 0.244 mm, respectively, compared with the traditional hand acupoints recognition algorithm without the operation of reflex zones and topology relationship stitching. Similarly, the error of the central punching point in the pericardial meridian area was also reduced by 0.286 mm.

These data indicate that the hand acupoint positioning method proposed in the implementations of the invention can effectively assist and improve the positioning accuracy of the acupoint. By splicing the reflex zones and topology relationship with the hand image, the acupoint recognition model can take into account both the direct features of the hand splicing image and the relevant reflex zone information, so as to better identify and locate each acupoint in the learning process.

Figure 11:
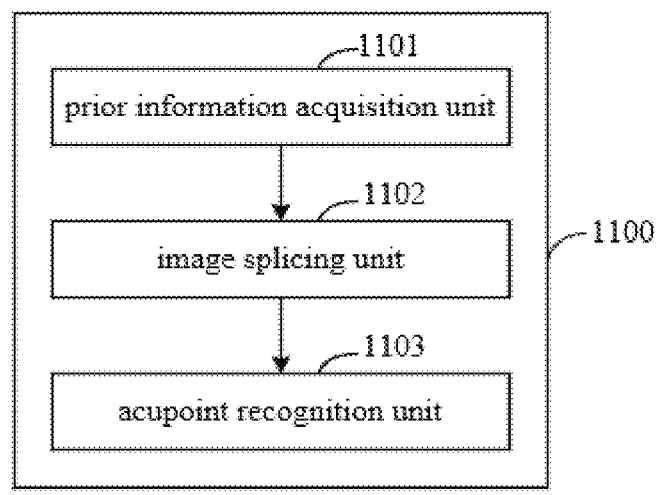
FIG. 11 is a structure diagram of an implementation of a hand acupoint positioning device.

In order to better implement the hand acupoint positioning method in the implementation of the invention, on the basis of the hand acupoint positioning method, the implementation of the invention also provides a hand acupoint positioning device. As shown in FIG. 11, the hand acupoint positioning device 1100, comprising:

prior information acquisition unit 1101, is used to obtain reflex zones of a hand image and the topology relationship of hand acupoints;

image splicing unit 1102, is used to splice the reflex zones, the topology relationship and the hand image to obtain a hand splicing image;

acupoint recognition unit 1103, is used to input the hand splicing image into an acupoint recognition model to obtain hand acupoints.

The hand acupoint positioning device 1100 can realize the technical scheme described in the above implementations of the hand acupoint positioning method, and the principles of the specific realization of the above modules or units can be referred to the corresponding contents in the above implementations of the hand acupoint positioning method.

It should be understood that before the monitoring begins, a baseline measurement is made to record the initial state of the qubit. This can be used as a reference point to compare subsequent measurements. Specifically, the qubit state measured in real time is compared with the benchmark measurement results. By comparing the change of qubit state, the change of bridge structure, such as stress distribution and damage location, can be analyzed.

Figure 12:
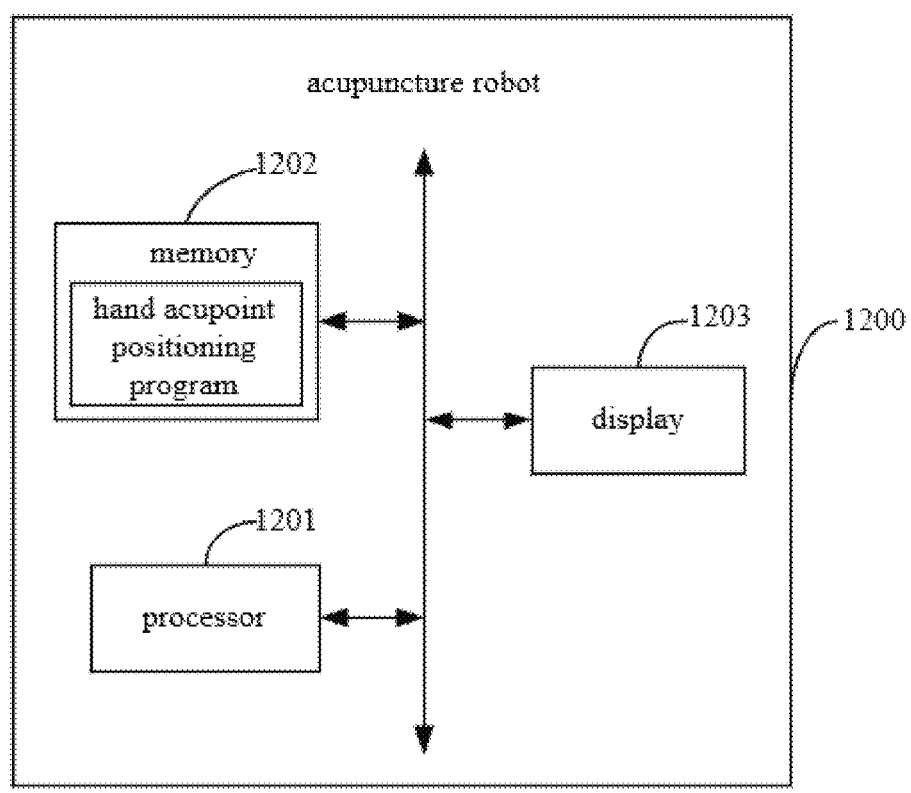
FIG. 12 is a structure diagram of an implementation of the acupuncture robot.

As shown in FIG. 12, the invention also correspondingly provides an acupuncture robot 1200. The acupuncture robot 1200 comprises a processor 1201, a memory 1202 and a display 1203. FIG. 12 shows only some of the components of the acupuncture robot 1200. It should be understood that it is not necessary to implement all of the components shown, and more or fewer components can be implemented instead.

In some implementations, the storage 1202 may be an internal storage unit of the acupuncture robot 1200, for example, a hard disk or a storage of the acupuncture robot 1200. In other implementations, the storage 1202 may be an external storage device of the acupuncture robot 1200, for example, a plug-in hard disk, a smart media card (SMC), a secure digital (SD) card, a flash card, etc. that are arranged on the acupuncture robot 1200.

Further, the storage 1202 may further includes both the internal storage unit of the acupuncture robot 1200 and the external storage device. The storage 1202 is used for storing and installing application software and various data of the acupuncture robot 1200.

The processor 1201 may in some implementations be a Central Processing Unit (CPU), microprocessor, or other data processing chip used to run program code stored in memory 1202 or to process data, such as the hand acupoint positioning method in the present invention.

In some implementations, the display 1203 may be an LED display, a liquid crystal display, a touch liquid crystal display, an organic light-emitting diode (OLED) touch screen, etc. The display 1203 is used for displaying information of the acupuncture robot 1200 and displaying a visual user interface. Parts 1201-1203 of the acupuncture robot 1200 communicate with each other through a system bus.

In some implementations of the present invention, when processor 1201 executes the hand acupoint positioning program in memory 1202, the following steps can be achieved:
obtaining reflex zones of a hand image and topology relationship of hand acupoints;
splicing the reflex zones, the topology relationship and the hand image to obtain a hand splicing image;
inputing the hand splicing image into an acupoint recognition model to obtain the hand acupoints.

It should be understood that: when executing the hand acupoint positioning program in the storage 1202, except the above functions, the processor 1201 can further implement other functions, which can be specifically seen in the descriptions of the previous related method implementations.

Accordingly, the present application implementation also provides a computer-readable storage medium for storing a computer-readable program or instruction that, when executed by the processor, is capable of realizing the steps or functions in the hand acupoint positioning method provided by the implementations of the above methods.

It is understood by those skilled in the art that all or part of the process to implement the above implementations may be accomplished by instructs the relevant hardware (e.g. processor, controller, etc.) through a computer program that may be stored in a computer readable storage medium. Among them, the computer readable storage medium is disk, optical disc, read-only storage memory or random storage memory.

The above hand acupoint positioning method, device, acupuncture robot and storage medium provided by the invention are introduced in detail. The principle and implementation mode of the invention are described in this paper with specific examples. The above implementation is only used to help understand the method and its core idea of the invention. At the same time, for the technical personnel in the field, according to the idea of the invention, there will be changes in the specific mode of implementation and scope of application, in summary, the content of this specification should not be understood as a limitation of the invention.

What is claimed is:

1. A hand acupoint positioning method, comprising:
obtaining reflex zones of a hand image and topology relationship of hand acupoints;
splicing the reflex zones, the topology relationship and the hand image to obtain a hand splicing image;
inputing the hand splicing image into an acupoint recognition model to obtain the hand acupoints;
wherein obtaining reflex zones of a hand image, comprising:
splitting the hand image based on a reflex zone segmentation model to obtain multiple initial reflex zones;
obtaining a plurality of key points of the hand image and determining whether the plurality of initial reflex zones are accurate based on the plurality of key points;
when the multiple initial reflex zones are accurate, the multiple initial reflex zones are taken as the reflex zones;
wherein obtaining the topology relationship of the hand acupoints, comprising:
obtaining multiple key points and hand acupoints of the hand image;
determining multiple first target key points that coincide with the hand acupoints in multiple key points, and multiple second target key points that do not coincide with the hand acupoints in multiple key points;
determining the topology relationship based on the multiple first target key points and the multiple second target key points.

2. The hand acupoint positioning method of claim 1, wherein the acupoint recognition model includes a feature extraction module, a feature fusion module and a detection module, wherein inputing the hand splicing image into the acupoint recognition model to obtain the hand acupoints, comprising:
extracting the features at different levels of the hand splicing image based on the feature extraction module to obtain a first feature map, a second feature map and a third feature map;
enhancing and fusing the first feature map, the second feature map and the third feature map based on the feature fusion module to obtain a first enhanced feature map, a second enhanced feature map and a third enhanced feature map;
detecting the first enhanced feature map, the second enhanced feature map and the third enhanced feature map based on the detection module to obtain the hand acupoints.

3. The hand acupoint positioning method of claim 2, wherein the feature extraction module includes a first feature extraction unit, three second feature extraction units and a space pyramid pool unit, the first feature extraction unit includes a first CBS layer, a second CBS layer and a first C2F layer, and the second feature extraction unit includes a third CBS layer and a second C2F layer, wherein extracting the features at different levels of the hand splicing image based on the feature extraction module to obtain a first feature map, a second feature map and a third feature map, comprising:
extracting the features of the hand splicing image based on the first feature extraction unit to obtain a initial feature map;
extracting the initial feature map based on the first second feature extraction unit to obtain the first feature map;
extracting the first feature map based on the second second feature extraction unit to obtain the second feature map;

extracting the second feature map based on the third second feature extraction unit and the space pyramid pooling unit to obtain the third feature map.

4. The hand acupoint positioning method of claim 2, wherein the feature fusion module includes two bottom-up first feature fusion units and two top-down second feature fusion units, the first feature fusion unit includes a first upsampling layer, a first splicing layer and a third C2F layer, and the second feature fusion unit includes a fourth CBS layer, a second splicing layer and a fourth C2F layer; wherein enhancing and fusing the first feature map, the second feature map and the third feature map based on the feature fusion module to obtain the first enhanced feature map, the second enhanced feature map and the third enhanced feature map, comprising:

fusing the third feature map and the second feature map based on the first first feature fusion unit to obtain a first fusion feature map;

fusing the first feature map and the first fusion feature map based on the second first feature fusion unit to obtain the first enhanced feature map;

fusing the first enhanced feature map and the first fusion feature map based on the first second feature fusion unit to obtain the second enhanced feature map;

fusing the third feature map and the second enhanced feature map based on the second second feature fusion unit to obtain the third enhanced feature map.

5. The hand acupoint positioning method of claim 2, wherein the detection module includes a parallel first detection unit, a second detection unit and a detection splicing unit, the first detection unit includes a fifth CBS layer and a first convolutional layer, and the second detection unit includes a sixth CBS layer and a second convolutional layer, the loss function of the first detection unit is VFL loss function, and the loss function of the second detection unit is CIoU and DFL Loss function.

6. A hand acupoint positioning device, is applicable to the hand acupoint positioning method of claim 1, and the hand acupoint positioning device, comprising:

prior information acquisition unit, is used to obtain reflex zones of a hand image and the topology relationship of hand acupoints;

image splicing unit, is used to splice the reflex zones, the topology relationship and the hand image to obtain a hand splicing image;

acupoint recognition unit, is used to input the hand splicing image into an acupoint recognition model to obtain hand acupoints.

7. An acupuncture robot, comprising memory and processor, among which, the memory is used to store a program;

the processor, coupled with the memory, is used to execute the program stored in the memory to implement the steps in the hand acupoint positioning method of claim 1.

8. A computer-readable storage medium is used to store a computer-readable program or instruction that, when executed by the processor, is capable of fulfilling the steps in the hand acupoint positioning method of claim 1.

* * * * *